United States Patent
Yamakoshi

(10) Patent No.: US 10,624,610 B2
(45) Date of Patent: Apr. 21, 2020

(54) ULTRASONIC IMAGING SYSTEM

(71) Applicant: National University Corporation Gunma University, Maebashi-shi (JP)

(72) Inventor: Yoshiki Yamakoshi, Maebashi (JP)

(73) Assignee: National University Corporation Gunma University, Maebashi-shi (JP)

( * ) Notice: Subject to any disclaimer, the term of this patent is extended or adjusted under 35 U.S.C. 154(b) by 458 days.

(21) Appl. No.: 15/301,283

(22) PCT Filed: Mar. 25, 2015

(86) PCT No.: PCT/JP2015/059207
§ 371 (c)(1),
(2) Date: Sep. 30, 2016

(87) PCT Pub. No.: WO2015/151972
PCT Pub. Date: Aug. 10, 2015

(65) Prior Publication Data
US 2017/0014104 A1    Jan. 19, 2017

(30) Foreign Application Priority Data
Apr. 2, 2014 (JP) ................................. 2014-076527

(51) Int. Cl.
*A61B 8/08* (2006.01)
*A61B 8/14* (2006.01)
(Continued)

(52) U.S. Cl.
CPC ............... *A61B 8/485* (2013.01); *A61B 8/06* (2013.01); *A61B 8/0833* (2013.01); *A61B 8/14* (2013.01);
(Continued)

(58) Field of Classification Search
CPC ......... A61B 8/485; A61B 8/14; A61B 8/5223; A61B 8/488
See application file for complete search history.

(56) References Cited

U.S. PATENT DOCUMENTS 5,919,139 A      7/1999 Lin
7,444,875 B1 *  11/2008 Wu .......................... A61B 8/08
                                                          73/602
(Continued)

FOREIGN PATENT DOCUMENTS

JP    2008-154012 A    7/2008
JP    2012-249776 A    12/2012
(Continued)

OTHER PUBLICATIONS

Wu et al. "Sonoelastographic imaging of interference patterns for estimation of the shear velocity of homogeneous biomaterials" Phys. Med. Biol. 49 (2004) 911-922.*
(Continued)

*Primary Examiner* — Bill Thomson
*Assistant Examiner* — Aminah Asghar
(74) *Attorney, Agent, or Firm* — Oblon, McClelland, Maier & Neustadt, L.L.P.

(57) ABSTRACT

An existing ultrasonic diagnostic device is used to obtain a color flow image of a target object whose stiffness is to be measured. At this time, a vibration exciter applies a micro vibration with a frequency of n/4 (n represents an odd number equal to or larger than 1) to the target object with respect to a burst frequency of an ultrasonic pulse to generate a shear elastic wave. As a result, a striped pattern corresponding to the stiffness of the target object caused by the shear elastic wave appears on a display of the ultrasonic diagnostic device as a shear elastic wave detection image.

5 Claims, 9 Drawing Sheets

(51) Int. Cl.
  *A61B 8/00* (2006.01)
  *A61B 8/06* (2006.01)
(52) U.S. Cl.
  CPC .............. *A61B 8/461* (2013.01); *A61B 8/488* (2013.01); *A61B 8/5223* (2013.01)

(56) References Cited

U.S. PATENT DOCUMENTS

| | | | |
|---|---|---|---|
| 9,125,547 B2* | 9/2015 | Xie | A61B 8/5223 |
| 9,986,973 B2* | 6/2018 | Chen | A61B 8/48 |
| 2004/0040379 A1* | 3/2004 | O'Donnell | A61B 5/0095 |
| | | | 73/627 |
| 2006/0052702 A1* | 3/2006 | Matsumura | A61B 8/08 |
| | | | 600/443 |
| 2009/0056453 A1 | 3/2009 | McAleavey | |
| 2010/0185090 A1* | 7/2010 | Suzuki | A61B 8/0858 |
| | | | 600/443 |
| 2012/0095323 A1* | 4/2012 | Eskandari | A61B 5/0051 |
| | | | 600/411 |
| 2013/0165778 A1 | 6/2013 | McAleavey | |
| 2013/0245442 A1* | 9/2013 | Hazard | G01S 7/52036 |
| | | | 600/438 |
| 2013/0261452 A1 | 10/2013 | Tamura | |
| 2013/0289402 A1* | 10/2013 | Tabaru | A61B 8/08 |
| | | | 600/438 |
| 2014/0018679 A1* | 1/2014 | Chen | A61B 8/085 |
| | | | 600/438 |
| 2014/0039317 A1 | 2/2014 | Sato | |
| 2014/0148697 A1 | 5/2014 | Barry et al. | |
| 2014/0180091 A1 | 6/2014 | McAleavey | |
| 2015/0272547 A1* | 10/2015 | Freiburger | A61B 8/485 |
| | | | 600/438 |
| 2016/0051231 A1* | 2/2016 | Kondo | A61B 8/485 |
| | | | 600/438 |
| 2017/0020486 A1* | 1/2017 | Salcudean | A61B 8/485 |

FOREIGN PATENT DOCUMENTS

| | | |
|---|---|---|
| JP | 2014-42823 A | 3/2014 |
| WO | WO 2008/141220 A1 | 11/2008 |
| WO | WO 2012/158877 A2 | 11/2012 |

OTHER PUBLICATIONS

Chen et al., "Shearwave Dispersion Ultrasound Vibrometry (SDUV) for Measuring Tissue Elasticitiy and Viscosity", IEEE Transactions on Ultrasonics, Ferroelectrics, and Frequency Control, vol. 56, No. 1, Jan. 2009 (Year: 2009).*

Bercoff et al., "Supersonic Shear Imaging: A New Technique for Soft Tissue Elasticity Mapping", IEEE Transactions on Ultrasonics, Ferroelectrics, and Frequency Control, vol. 51, No. 4, Apr. 2004 (Year: 2004).*

Raj Kumar Parajuli et al 2013 Jpn. J. Appl. Phys. 52 07H F22 (Year: 2013).*

N. Masuda, et al., "Low-Frequency Elastic Wave Imaging by Adaptive Combination of Fundamental and Tissue Harmonic Ultrasonic Waves," Japanese Journal of Applied Physics, vol. 42, Part 1, No. 5B, May 1, 2003, 5 pages (with English abstract).

International Search Report dated Jun. 23, 2015 in PCT/JP2015/059207 Filed Mar. 25, 2015.

Extended European Search Report dated Dec. 22, 2017 in Patent Application No. 15773342.9, citing documents AC-AF, AO, AP and AX therein, 8 pages.

Yoshiki Yamakoshi, et al., "Ultrasonic Imaging of Internal Vibration of Soft Tissue under Forced Vibration" IEEE, Transactions on Ultrasonics, Ferroelectrics and Frequency Control, vol. 37, No. 2, XP011438071, Mar. 1, 1990, pp. 45-53.

* cited by examiner

BASIC OPERATOR 1

$U = I_i Q_{i+1} - I_{i+1} Q_i$

BASIC OPERATOR 2

$L = I_{i+1} I_i + Q_{i+1} Q_i$

ULTRASONIC IMAGING SYSTEM

TECHNICAL FIELD

The present invention relates to an ultrasonic imaging system mainly for medical application, the ultrasonic imaging system being adapted to use an ultrasonic wave to form a cross-sectional image of a subject in a non-invasive manner.

BACKGROUND ART

An ultrasonic diagnostic device emits an ultrasonic wave generated by an ultrasonic transducer built-in an ultrasonic probe toward a subject, and receives, with the ultrasonic transducer, a reflected signal generated due to the difference in acoustic impedance of the tissue of the subject. Further, the reflected signal is subjected to an arithmetic processing, such as Fourier transform, to form an image to be displayed on a display. Since such ultrasonic diagnostic device can easily observe a two-dimensional image of the tissue of the subject in real time by performing a simple and non-invasive operation of contacting the ultrasonic probe onto the surface of the subject, it is widely used for performing function test of a heart or the like, and shape diagnostics of various organs. Particularly, since almost no radiation injury is caused to the subject, such diagnostic imaging method is essential for performing fetus growth diagnostic.

The PLT 1 and NPL 1 listed below are prior arts close to the technical field of the present invention.

PLT 1 discloses technical contents of a method and system for imaging a three-dimensional ultrasonic scattering medium in a subject volume.

NPL 1 discloses technical contents of an exciting imaging method for estimating the propagation velocity of the phase change of a low-frequency vibration applied from outside.

CITATION LIST

Patent Literature

PTL 1: Japanese Unexamined Patent Application Publication No. 2008-154012

Non Patent Literature

NPL 1: "Elastic wave imaging by adaptive combination of fundamental and tissue harmonic ultrasonic waves" by Masuda Nobuyuki, Tsujita Takehiro, Ebuchi Tomoaki, Yamakoshi Yoshiki, published in a symposium on ultrasonic electronics (23), accessible at: http://ci.nii.ac.jp/naid/110007464507 (searched on Apr. 23, 2013)

SUMMARY OF INVENTION

Technical Problem

Evaluation of stiffness of body tissue is attracting increasing attention, particularly in diagnostic areas of liver, mammary gland, prostate gland and the like where the stiffness of the tissue has close relationship with diseases. Further, in the orthopedic surgery, if function of skeletal muscle can be evaluated from the stiffness, it will be helpful for diagnosing diseases related to skeletal muscle, such as muscular dystrophy, and helpful for performing intraoperative evaluation for tendon repair treatment.

In a frequency of an ultrasonic wave, compressional elastic wave is predominant; therefore, almost all conventional ultrasonic diagnostic devices do not have a function to measure the stiffness of body tissue. The compressional elastic wave is a wave whose vibration direction is parallel to the transmission direction of the vibration in the medium. The compressional elastic wave is a wave accompanied by volume change of the medium, and is equivalent to a P-wave associated with vertical vibration, if taking earthquake as an analogy. Since the transmission speed of the compressional elastic wave almost does not depend on the stiffness of the medium, it is extremely difficult to detect the stiffness of the medium with an ultrasonic diagnostic device that uses an ultrasonic wave as it is.

In techniques for measuring the stiffness of the body tissue, there are two types of techniques known as below.

The first technique is called "elastography" that is a method in which the portion where the stiffness is to be measured of the subject is pressed by a hand or the like, and deformation of the tissue caused by the pressure is measured from an ultrasonic image.

The second technique is a method in which the portion where the stiffness is to be measured is irradiated by a high intensity ultrasonic pulse, and an acoustic radiation pressure caused by the pulse excites a shear elastic wave in the body tissue. Further, Doppler frequency shift signal of the ultrasonic wave caused by the shear elastic wave generated in the body tissue is detected to measure the stiffness of the body tissue. Incidentally, in the description of the present invention, such method is called "acoustic radiation pressure method". The shear elastic wave is also called "shear wave", and is a wave whose vibration direction is perpendicular to the propagation direction of the vibration in the medium. The shear elastic wave is a wave not accompanied by volume change of the medium, and is equivalent to an S-wave associated with lateral vibration, if taking earthquake as an analogy. The propagation speed of the shear elastic wave largely depends on the stiffness of the medium.

The advantage of the elastography method is that the measurement principle thereof is simple, and the disadvantage is that it has poor quantitativeness and that the measurement accuracy depends on the skill of the operator.

The advantage of the acoustic radiation pressure method is that it is possible to perform quantitative measurement; however, since heat will be generated in the body tissue due to the radiation of the high intensity ultrasonic wave, there is a safety concern for human body.

In view of the aforesaid problems, an object of the present invention is to provide an ultrasonic imaging system capable of imaging the stiffness of the object-to-be-measured easily and safely simply by adding an extremely simple device to a conventional ultrasonic diagnostic device.

Solution to Problem

To solve the aforesaid problems, an ultrasonic imaging system according to an aspect of the present invention comprises an ultrasonic image forming device capable of outputting a color flow image which renders a fluid existing within an object-to-be-measured by: outputting an ultrasonic pulse for measuring the inside structure of the object-to-be-measured in a non-invasive manner, emitting the ultrasonic pulse from an ultrasonic probe for receiving the ultrasonic pulse, and receiving the ultrasonic pulse; and a shear elastic wave generator that applies a vibration with a predetermined frequency to the object-to-be-measured.

Advantageous Effects of Invention

According to the present invention, it is possible to image the stiffness of the object-to-be-measured easily and safely simply by adding an extremely simple device to a conventional ultrasonic diagnostic device.

Other problems, configurations and effects than those described above will be known from the description of the following embodiment.

DESCRIPTION OF EMBODIMENTS

In a vibration, the ratio of compressional elastic wave to shear elastic wave varies according to the frequency of the vibration. The lower the frequency is, the more dominant the shear elastic wave will become.

Generally, the propagation velocity of the shear elastic wave is proportional to the square root of the stiffness of the medium. Therefore, it becomes possible to measure the stiffness of an object-to-be-measured if it is possible to apply a shear elastic wave to the object-to-be-measured and detect the propagation velocity of the shear elastic wave.

In an ultrasonic imaging system according to an embodiment of the present invention, a color flow image display function (which is adapted to detect existence and velocity of a fluid within a tissue) provided by an ultrasonic diagnostic device is used to display the wave front of the shear elastic wave as an image.

[Entire Configuration of Ultrasonic Imaging System 101]

Figure 1:
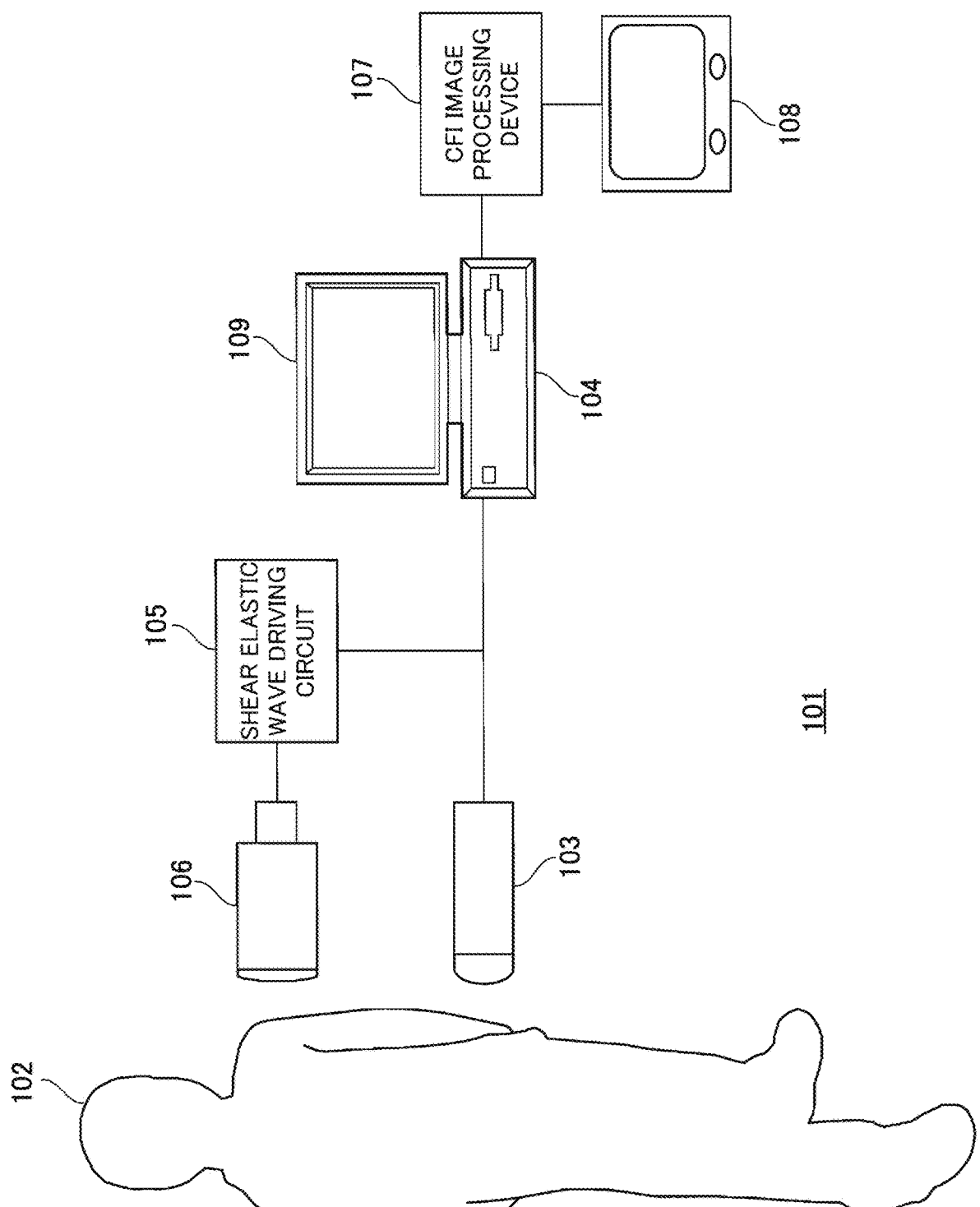
FIG. 1 is a block diagram showing the entire configuration of an ultrasonic imaging system according to an embodiment of the present invention.

FIG. 1 is a block diagram showing the entire configuration of an ultrasonic imaging system 101 according to the embodiment of the present invention.

The ultrasonic imaging system 101 is configured by adding a shear elastic wave driving circuit 105, a vibration exciter 106 (which is excited by the shear elastic wave driving circuit 105), a CFI image processing device 107, and a display device 108 to an ultrasonic diagnostic device 104 (i.e., an ultrasonic image forming device) which is provided with an ultrasonic probe 103 for emitting ultrasonic pulse to a subject 102. Incidentally, the CFI image processing device 107 and display device 108 may also be omitted, so that only the shear elastic wave driving circuit 105 and vibration exciter 106 are added to the ultrasonic diagnostic device 104. In such a case, an image including a characteristic striped pattern caused by the shear elastic wave is displayed on a display 109 of the ultrasonic diagnostic device 104, though the image is mixed with noises. The stiffness of the body tissue of the subject 102 can be estimated based on the intervals of the striped pattern. The image of the striped pattern caused by the shear elastic wave and displayed on the display 109 of the ultrasonic diagnostic device 104 is hereinafter referred to as a "shear elastic wave detection image". An image obtained by processing the data of the shear elastic wave detection image with the CFI image processing device 107 and displaying the result as an image on the display device 108 is hereinafter referred to as a "shear elastic wave display image".

The ultrasonic diagnostic device 104 has a function of outputting a "B-mode image" (i.e., a function of outputting an ultrasonic pulse from the ultrasonic probe 103, and shows the existence of the inside of the body tissue as a black-and-white image). In addition to the function of outputting the "B-mode image", the ultrasonic diagnostic device 104 also has a function of outputting a "color flow image", which is also called "color flow mapping" (i.e., a function of detecting Doppler effect generated by the bloodstream flowing in the blood vessels, dividing the bloodstream colors, and displaying the results over the B-mode image). The ultrasonic pulse is a burst wave obtained by outputting a high frequency ultrasonic wave with a frequency of about 1 MHz or higher at a cycle of, for example, 365 Hz. Hereinafter, a frequency corresponding to the cycle of the ultrasonic pulse is referred to as a "burst frequency".

The vibration exciter 106 generates a low frequency micro vibration under a drive voltage outputted by the shear elastic wave driving circuit 105. The content of the vibration exciter 106 is a piezoelectric element, and the details of the vibration exciter 106 will be discussed later with reference to FIG. 2. Obviously, the vibration exciter may also be an electromagnetically driven vibration exciter similar to a widely known speaker.

The shear elastic wave driving circuit 105 generates a shear elastic wave with a frequency satisfying Equation (1) and an amplitude satisfying Equation (2), with respect to the burst frequency of the ultrasonic pulse supplied from the ultrasonic diagnostic device 104 to the ultrasonic probe 103.

[Mathematical Expression 1]

$$f_b = \frac{1}{2}\left(m + \frac{1}{2}\right)f_e \qquad (1)$$

where:

m represents an integer equal to or greater than 0

$f_e$ represents burst frequency $$\frac{\lambda}{8} \le \xi_0 \le \frac{3\lambda}{8} \qquad (2)$$

where:

λ represents wavelength of ultrasonic wave

ξ represents vibration amplitude of shear elastic wave

For example, in the case where the burst frequency is 365 Hz, the frequency of the shear elastic wave will be:

91.25 Hz, when m=0;
273.75 Hz, when m=1;
456.25 Hz, when m=2;
638.75 Hz, when m=3.

In other words, the frequency of the shear elastic wave is obtained by multiplying the burst frequency by a fraction: ¼, ¾, ⁵⁄₄, ⁷⁄₄ . . . , where the denominator of the fraction is 4, and the numerator of the fraction is an odd number starting from 1.

For example, in the case where the center frequency of the ultrasonic pulse is 5 MHZ, the amplitude of the shear elastic wave depends on the propagation velocity of the medium propagated by the shear elastic wave, and excellent shear elastic wave detection image and shear elastic wave display image can be obtained when the vibration exciter 106 is vibrated at an amplitude of 100 microns, for example.

When causing the vibration exciter 106 to generate a shear elastic wave having a frequency satisfying Equation (1) and abutting the vibration exciter 106 to a measurement part of the subject 102 (wherein the measurement part is near to a portion brought into contact with the ultrasonic probe 103), a striped pattern depending on the stiffness of the body tissue appears on the color flow image (which shows bloodstream) displayed on the display 109 of the ultrasonic diagnostic device 104. The interval of the striped pattern corresponds to the wavelength of the shear elastic wave within the body tissue. Since the propagation velocity of the shear elastic wave is generally proportional to the square root of the stiffness of the medium, the stiffness of the body tissue can be estimated by measuring the intervals of the striped pattern.

Figure 2:
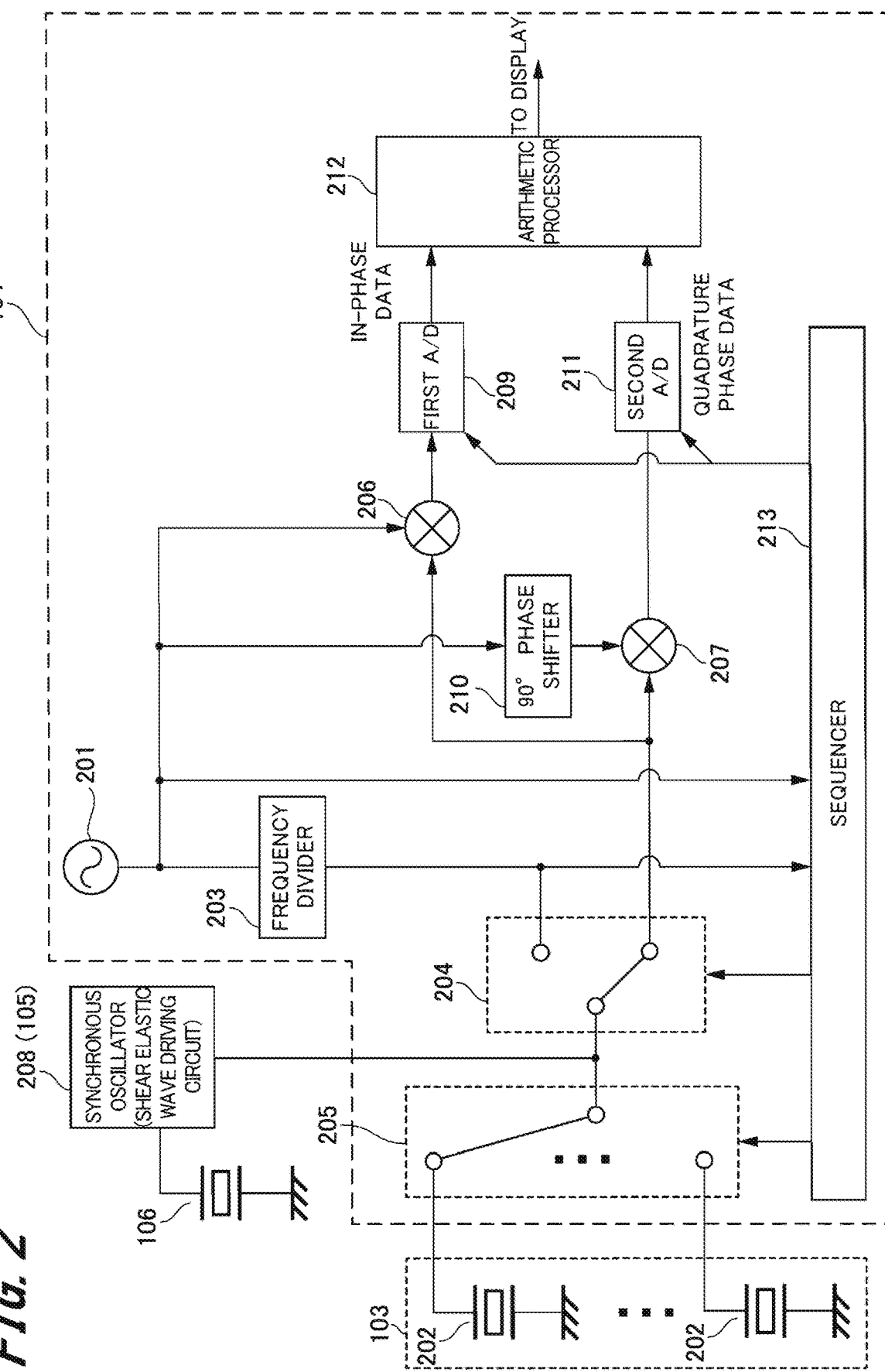
FIG. 2 is a functional block diagram of the ultrasonic diagnostic device.

In order to display an excellent shear elastic wave detection image, the phase difference of the shear elastic wave outputted from the shear elastic wave driving circuit 105 with respect to the edges of the ultrasonic pulse may be maintained within a desired error range. FIGS. 1 and 2 are made based on an assumption that the shear elastic wave outputted from the shear elastic wave driving circuit 105 is synchronized with edges of the ultrasonic pulse; however, the shear elastic wave and the edges of the ultrasonic pulse do not have to be synchronized with each other if the burst frequency of the ultrasonic pulse and the frequency of the shear elastic wave have sufficient accuracy.

FIG. 2 is a functional block diagram of the ultrasonic diagnostic device 104.

The oscillator 201 outputs a drive signal of the center frequency of the ultrasonic probe 103 coming from a plurality of ultrasonic transducers 202 provided within the ultrasonic probe 103. The center frequency of the ultrasonic wave is 5 MHz, for example. The entity of each ultrasonic transducer 202 is a piezoelectric element. The piezoelectric element deforms when voltage is applied thereto, and the piezoelectric element generates a voltage when being deformed. The signal outputted from the oscillator 201 is supplied to a frequency divider 203. The frequency divider 203 generates an ultrasonic pulse with a predetermined burst frequency based on the drive signal. The center frequency of the ultrasonic pulse is 365 Hz, for example. The ultrasonic pulse outputted from the frequency divider 203 is selectively supplied to the plurality of ultrasonic transducers 202 through a first multiplexer 204 and a second multiplexer 205.

The first multiplexer 204 is adapted to switch transmission and reception of the ultrasonic probe 103. When performing transmission, the first multiplexer 204 connects the ultrasonic probe 103 to the frequency divider 203; while when performing reception, the first multiplexer 204 connects the ultrasonic probe 103 to a first multiplier 206 and a second multiplier 207.

The second multiplexer 205 is adapted to select one of the plurality of ultrasonic transducers 202 housed in the casing of the ultrasonic probe 103.

On the other hand, the ultrasonic pulse is also supplied to a synchronous oscillator 208 through the first multiplexer 204. The synchronous oscillator 208 is the entity of the shear elastic wave driving circuit 105. The synchronous oscillator 208 outputs a drive voltage with a frequency satisfying the aforesaid Equation (1) with respect to the burst frequency of the ultrasonic pulse. The drive voltage drives the piezoelectric element built in the vibration exciter 106.

Incidentally, a high voltage required to drive the piezoelectric element used for the ultrasonic probe 103 and the vibration exciter 106; due to limited space of the drawings, description about the high voltage generating means is omitted in FIG. 2.

The reception-side terminal of the first multiplexer 204 is connected to the first multiplier 206 and second multiplier 207 which configure a quadrature detector.

The first multiplier 206 multiplies a reception signal outputted from the ultrasonic probe 103 by the drive signal. The signal outputted from the first multiplier 206 is supplied to a first A/D converter 209 (which is referred to as "first A/D" in FIG. 2) where the signal is subjected to an A/D conversion. The output data of the first A/D converter 209 is "in-phase data" corresponding to a real number component. The in-phase data is supplied to an arithmetic processor 212.

The second multiplier 207 multiplies a reception signal outputted from the ultrasonic probe 103 by a drive signal whose phase has been delayed by 90° by a phase shifter 210. The signal outputted from the second multiplier 207 is supplied to a second A/D converter 211 (which is referred to as "second A/D" in FIG. 2) where the signal is subjected to an A/D conversion. The output data of the second A/D converter 211 is "quadrature phase data" corresponding to an imaginary component. The quadrature phase data is supplied to the arithmetic processor 212.

Figure 3:
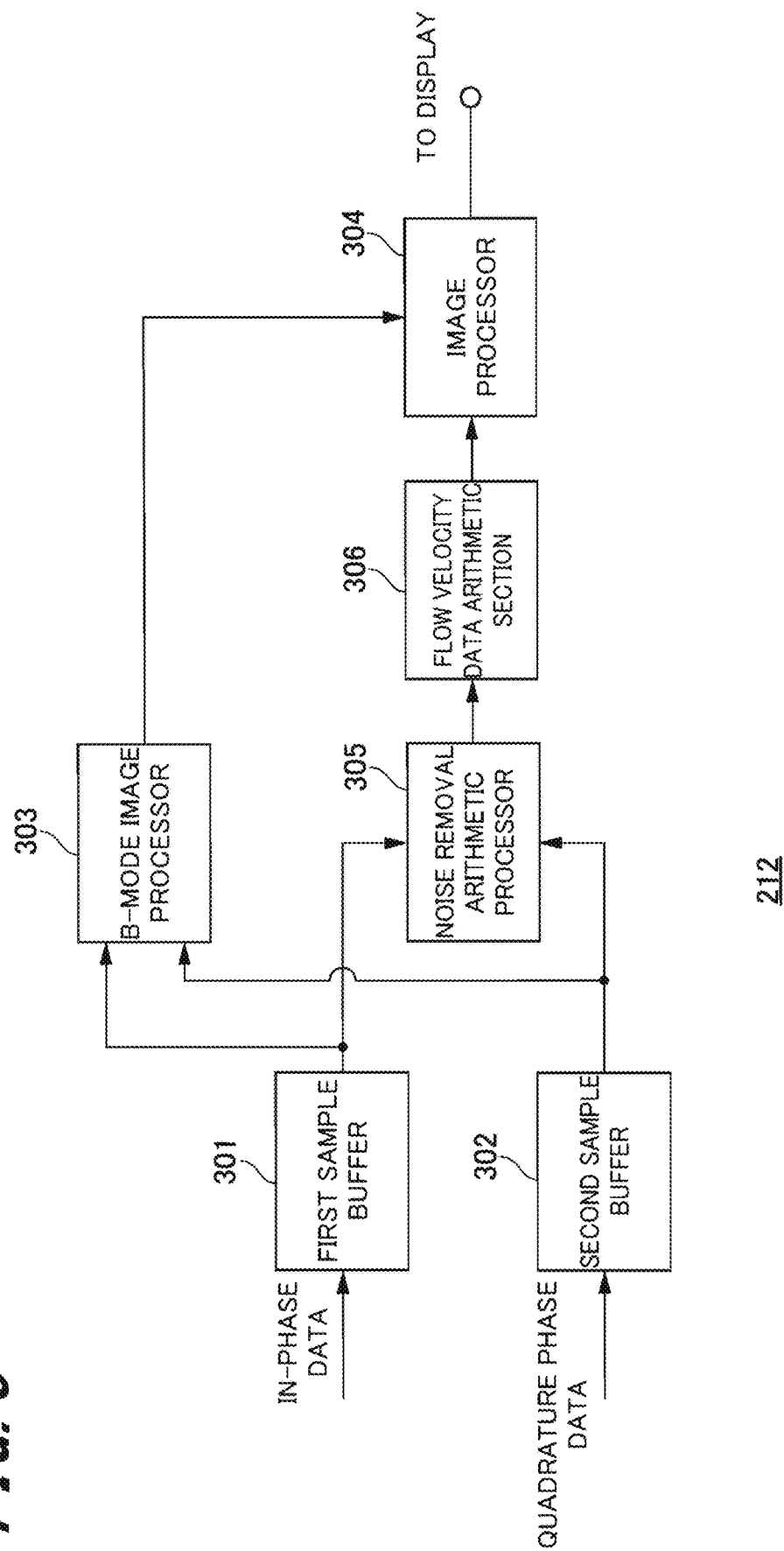
FIG. 3 is a functional block diagram of an arithmetic processor.

FIG. 3 is a functional block diagram of the arithmetic processor 212.

The in-phase data is once stored in a first sample buffer 301, which is configured by a widely known RAM.

Similarly, the quadrature phase data is also once stored in a second sample buffer 302, which is configured by a widely known RAM.

The in-phase data stored in the first sample buffer 301 and the quadrature phase data stored in the second sample buffer 302 are subjected to an arithmetic processing for generating a B-mode image performed by a B-mode image processor 303, wherein the in-phase data and the quadrature phase data each have a predetermined duration. The arithmetic processing is a processing for generating a black-and-white image mainly by means of FFT (fast Fourier transform). The B-mode image data generated by the B-mode image processor 303 is supplied to an image processor 304.

On the other hand, the in-phase data stored in the first sample buffer 301 and the quadrature phase data stored in the second sample buffer 302, each having a predetermined duration, are subjected to a noise removing processing performed by a noise removal arithmetic processor 305, and a signal component associated with Doppler effect of bloodstream is extracted. The signal component associated with Doppler effect is converted into color flow image data by a flow velocity data arithmetic section 306, and the color flow image data is supplied to the image processor 304.

The image processor 304 superimposes the B-mode image data and the color flow image data, and outputs the superimposed data to the display 109.

[Principle of Shear Elastic Wave Detection Image]

FIGS. 2 and 3 explain a functional block of a conventional ultrasonic diagnostic device 104 capable of using the ultrasonic pulse to output a color flow image. In the ultrasonic imaging system 101 of the present embodiment, a shear elastic wave detection image can be obtained simply by adding the vibration exciter 106 to the ultrasonic diagnostic device 104, wherein the vibration exciter 106 vibrates at a frequency satisfying Equation (1) and a vibration amplitude satisfying Equation (2). The principle of displaying the shear elastic wave detection image on the display 109 of the ultrasonic diagnostic device 104 is described below.

<Flow Velocity Estimation Algorithm of Color Flow Image>

A flow velocity estimation algorithm, which is the base of the color flow image outputted from the ultrasonic diagnostic device 104 and indicating the velocity of a fluid, will be described first.

Here, when N ultrasonic pulses are transmitted to an arbitrary fluid in the same direction, the phase $\Phi_i$ of a reception ultrasonic wave corresponding to the i-th ultrasonic pulse can be expressed as the following Equation (3).

[Mathematical Expression 2]

$$\phi_i = \phi_0 + \frac{2\pi f_0}{c} 2vi\Delta t \quad (3)$$

where:
$\Phi_0$ represents initial phase
$f_0$ represents center frequency of ultrasonic wave
c represents sound velocity
v represents flow velocity
$\Delta t$ represents interval between two adjacent ultrasonic pulses According to Equation (3), an i-th reception RF signal can be expressed as the following Equation (4).

[Mathematical Expression 3]

$$r_i = r_0 \sin(2\pi f_0 t + \phi_i) \quad (4)$$
$$= r_0 \sin\left(2\pi f_0 t + \phi_0 + \frac{2\pi f_0}{c} 2vi\Delta t\right)$$

When the reception RF signal of Equation (4) is subjected to a quadrature detection performed by a quadrature detector, its complex quadrature detection output $\vec{Q}_i$, as well as an in-phase signal $I_i$ (which is a real part signal of $\vec{Q}_i$) and a quadrature phase signal $Q_i$ (which is an imaginary part signal of $\vec{Q}_i$) can be expressed as the following Equation (5).

$$\vec{Q}_i = I_i + jQ_i \quad (5)$$

$$\begin{cases} I_i = a\cos\left(\phi_0 + \frac{2\pi f_0}{c} 2vi\Delta t\right) \\ Q_i = a\sin\left(\phi_0 + \frac{2\pi f_0}{c} 2vi\Delta t\right) \end{cases}$$

Equation (5) may also be written as the following Equation (6).

[Mathemaical Expression 5]

$$\vec{Q}_i = a\exp\left(j\left(\phi_0 + \frac{2\pi f_0}{c} 2vi\Delta t\right)\right) \quad (6)$$

Here, a difference $\Delta\Phi_0$ between the phase of the ultrasonic pulse and the phase of the (i+1)-th ultrasonic pulse can be estimated as the following Equation (7).

[Mathematical Expression 6]

$$\Delta\phi_i = \arg(\vec{Q}_{i+1}\vec{Q}_i^*) \quad (7)$$

Since the difference $\Delta\Phi_i$ between the phases of the ultrasonic pulse can be estimated as Equation (7), the following Equation (8) can be obtained when Equation (6) is substituted into Equation (7).

[Mathematical Expression 7]

$$\Delta\phi_i = \arg\left(a^2 \exp\left(j\frac{2\pi f_0}{c} 2v\Delta t\right)\right) \quad (8)$$
$$= \frac{2\pi f_0}{c} 2v\Delta t$$

Thus, the flow velocity v can be obtained by the following Equation (9).

[Mathematical Expression 8]

$$v = \frac{c}{2\pi f_0 \cdot 2\Delta t} \Delta\phi_i = \frac{c}{2\pi f_0 \cdot 2\Delta t} \arg(\vec{Q}_{i+1}\vec{Q}_i^*) \quad (9)$$

If an IQ signal is used, the part in the parentheses of Equation can be expressed as the following Equation (10).

[Mathematical Expression 9]

$$\vec{Q}_{i+1}\vec{Q}_i^* = (I_{i+1} + jQ_{i+1})(I_i + jQ_i)^* \quad (10)$$
$$= (I_{i+1} + jQ_{i+1})(I_i - jQ_i)$$
$$= I_{i+1}I_i + Q_{i+1}Q_i + j(I_i Q_{i+1} - I_{i+1} Q_i)$$

From Equation (10), the following Equation (11) can be derived as an equation for estimating flow velocity.

[Mathematical Expression 10]

$$v = \frac{c}{2\pi f_0 \cdot 2\Delta t} \arctan\left(\frac{I_i Q_{i+1} - I_{i+1} Q_i}{I_{i+1} I_i + Q_{i+1} Q_i}\right) \quad (11)$$

In the color flow image of the ultrasonic diagnostic device 104, in order to increase S/N, a quadrature detection output signal obtained from N consecutive ultrasonic pulses is used to estimate the flow velocity with the following Equation (12).

[Mathematical Expression 11]

$$v = \frac{c}{2\pi f_0 \cdot 2\Delta t} \arctan\left(\frac{E_U}{E_L}\right) \quad (12)$$

$$\begin{cases} E_U = \sum_{i=1}^{N} I_i Q_{i+1} - I_{i+1} Q_i \\ E_L = \sum_{i=1}^{N} I_{i+1} I_i + Q_{i+1} Q_i \end{cases}$$

<Wave Front Detection of Shear Elastic Wave with Flow Velocity Estimation Algorithm of Color Flow Image>

Here, the flow velocity estimation algorithm of the ultrasonic diagnostic device 104 is applied to a case where the shear elastic wave causes a reflector vibrate sinusoidally.

When the shear elastic wave propagates so that the tissue vibrates sinusoidally, the tissue displacement ξ can be expressed as the following Equation (13).

[Mathematical Expression 12]

$$\xi = \xi_0 \sin(\omega_b t + \phi_b) \quad (13)$$

Where $\omega_b$ represents vibration angular frequency $\Phi_b$ represents initial phase At this time, the phase $\Phi_i$ of the i-th reception ultrasonic pulse can be expressed as the following Equation (14).

[Mathematical Expression 13]

$$\phi_i = \phi_0 + \frac{2\pi f_0}{c} 2\xi \quad (14)$$

Similar to Equation (5), the output of the quadrature detector can be expressed as the following Equation (15).

[Mathematical Expression 14]

$$\begin{cases} I_i = a\cos\left(\phi_0 + \frac{2\pi f_0}{c} 2\xi\right) \\ Q_i = a\sin\left(\phi_0 + \frac{2\pi f_0}{c} 2\xi\right) \end{cases} \quad (15)$$

Here, it is considered that a condition (frequency condition) expressed as the following Equation (16) is satisfied with respect to the angular frequency of the shear elastic wave.

[Mathematical Expression 15]

$$\omega_b = \frac{2\pi}{4\Delta t} \quad (16)$$

In other words, the frequency of the shear elastic wave can be expressed as the following Equation (17).

[Mathematical Expression 16]

$$f_b = \frac{1}{4\Delta t} \quad (17)$$

Further, the initial phase of the vibration satisfies the following Equation (18).

[Mathematical Expression 17]

$$\phi_b 0 \quad (18)$$

Figure 4:
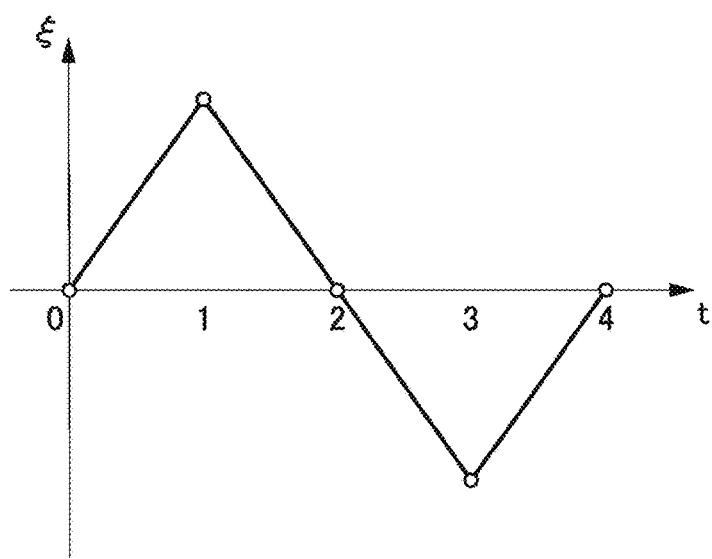
FIG. 4 a graph showing a relationship between the cycle and displacement amplitude of a displacement vibration of a tissue caused by the propagation of a shear elastic wave.

The aforesaid condition (i.e., Equations (17) and (18)) is a condition that the cycle of the displacement vibration of the tissue caused by the propagation of the shear elastic wave is equal to 4 pulses of the ultrasonic wave and that the initial phase is 0; such condition can be illustrated as FIG. 4.

FIG. 4 is a graph showing a relationship between the cycle and displacement amplitude of the displacement vibration of the tissue caused by the propagation of the shear elastic wave.

The vibration amplitude identical to that of FIG. 4 is also generated in the case where a shear elastic wave with high vibration frequency is folded in a low frequency by aliasing; and at this time, the vibration frequency can be expressed as the following Equation (19), which is Equation (1), where m represents an integer.

[Mathematical Expression 18]

$$f_b = \frac{1}{2}\left(m + \frac{1}{2}\right)\frac{1}{\Delta t} \quad (19)$$

Thus, since the following discussion is also applied to a case where Equation (19) is satisfied, the frequency of the shear elastic wave may satisfy Equation (19). Equation (19) (which is equal to Equation (1)) represents a frequency condition for imaging the shear elastic wave on the ultrasonic diagnostic device 104.

At this time, the displacement can be expressed as the following Equation (20).

[Mathematical Expression 19]

$$\xi = \xi_0 \sin(2\pi f_b i \Delta t) \quad (20)$$

At this time, I, Q signals, which are the output signals of the quadrature detector, are expressed as the following Equation (21).

[Mathematical Expression 20]

$$\begin{cases} I_i = a\cos\left(\frac{4\pi f_0}{c}\xi\right) \\ Q_i = a\sin\left(\frac{4\pi f_0}{c}\xi\right) \end{cases} \quad (21)$$

Here, in the case where I=0, 1, 3, the output of the quadrature detector is obtained as the following Equations (22), (23), (24), (25), (26), and (27).

[Mathematical Expression 21]

When $i = 0$ (22)
$$\begin{cases} I_i = a \\ Q_i = 0 \end{cases}$$

When i=1

$$I_i = a\cos\left(\frac{4\pi f_0}{c}\xi_0\right) \quad (23)$$

however, if $\lambda$ is wavelength of ultrasonic wave (1) when $0 \leq \xi_0 \leq \frac{\lambda}{8}$ $\begin{cases} I_i \geq 0 \\ Q_i \geq 0 \end{cases}$ (24)

(2) when $\frac{\lambda}{8} \leq \xi_0 \leq \frac{3\lambda}{8}$ $\begin{cases} I_i \leq 0 \\ Q_i \geq 0 \end{cases}$ When i=2

$$\begin{cases} I_i = a \\ Q_i = 0 \end{cases} \quad (25)$$

When i=3

$$I_i = a\cos\left(\frac{4\pi f_0}{c}\xi_0\right) \quad (26)$$

however (1) when $0 \leq \xi_0 \leq \frac{\lambda}{8}$ $\begin{cases} I_i \geq 0 \\ Q_i \leq 0 \end{cases}$ (27)

Figure 5A:
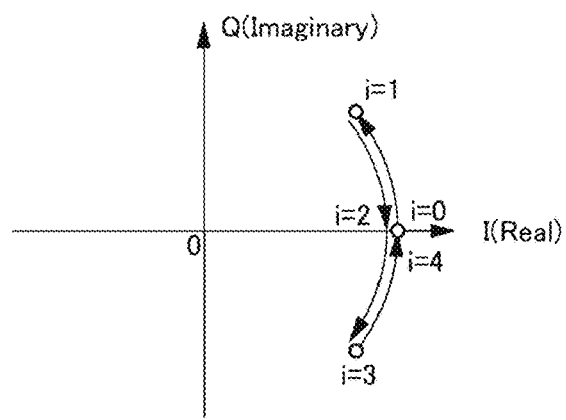
FIGS. 5A and 5B are vector diagrams showing the relationship between amplitudes of an output signal of a quadrature detector for each i-th sample value.
Figure 5B:
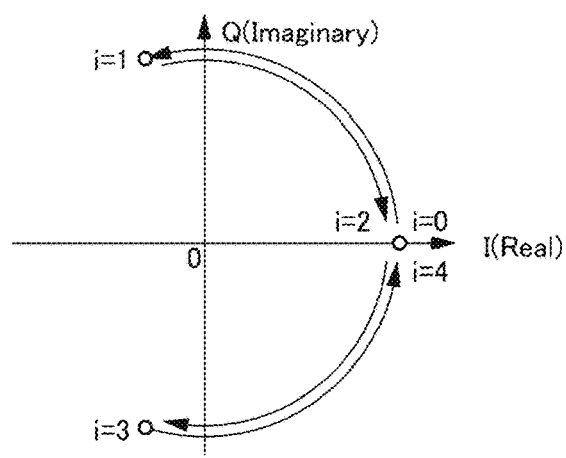

(2) when $\frac{\lambda}{8} \leq \xi_0 \leq \frac{3\lambda}{8}$ $\begin{cases} I_i \leq 0 \\ Q_i \leq 0 \end{cases}$ The relationship between Equations (23) to (27) can be expressed as vector diagrams shown in FIGS. 5A and 5B.

FIGS. 5A and 5E are vector diagrams showing the relationship between the amplitudes of the output signal of the quadrature detector for each i-th sample value.

FIG. 5A is a vector diagram in the case where the vibration amplitude $\xi_0$ satisfies "$0 \leq \xi_0 \leq \lambda/8$".

As shown in FIG. 5A, all vectors fall within the first and fourth quadrants.

FIG. 5B is a vector diagram in the case where the vibration amplitude $\xi_0$ satisfies "$\lambda/8 \leq \xi_0 \leq 3\lambda/8$".

As shown in FIG. 5B, when i=1 or 3, the vector falls within the second or third quadrant.

The above discussion is compiled in Table 1.

TABLE 1

| Output signal of quadrature detector | | |
|---|---|---|
| i | $I_i$ | $Q_i$ |
| 0 | a | 0 |
| 1 | $I_a$ | $Q_a$ (positive) |
| 2 | a | 0 |
| 3 | $I_a$ | $-Q_a$ (negative) |

$$\begin{cases} \text{when } 0 \leq \xi_0 \leq \frac{\lambda}{8} & I_a \geq 0 \\ \text{when } \frac{\lambda}{8} \leq \xi_0 \leq \frac{3\lambda}{8} & I_a \leq 0 \end{cases}$$

Next, the estimated flow velocity of the ultrasonic diagnostic device 104 with respect to the patterns shown in the above Table 1 is obtained as below.

First, the flow velocity derivation algorithm expressed as Equation (12) is modeled with two basic operators.

Figure 6A:
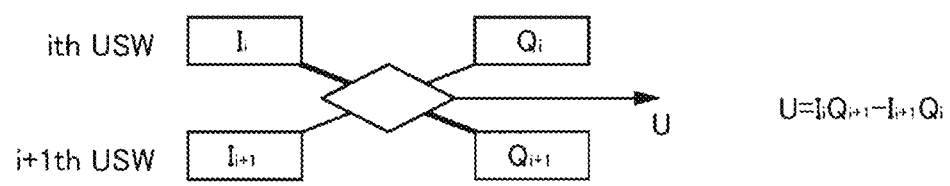
FIGS. 6A and 6B are model diagrams respectively showing a first basic operator and a second basic operator.
Figure 6B:
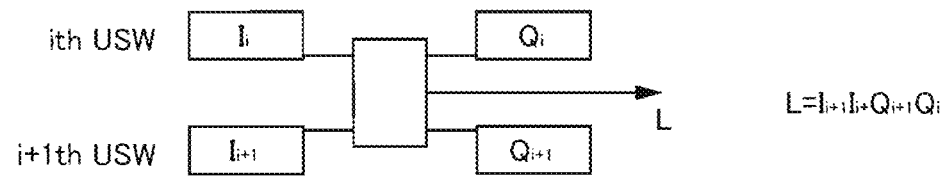

FIG. 6A is a model diagram showing a first basic operator. FIG. 6B is a model diagram showing a second basic operator.

First, the i-th in-phase data and quadrature phase data and the (i+1)-th in-phase data and quadrature phase data are prepared as the outputs of the quadrature detector.

The first basic operator is an operator of a stage before the summation for deriving $E_U$ in Equation (12).

The second basic operator is an operator of a stage before the summation for deriving $E_L$ in Equation (12).

Figure 7A:
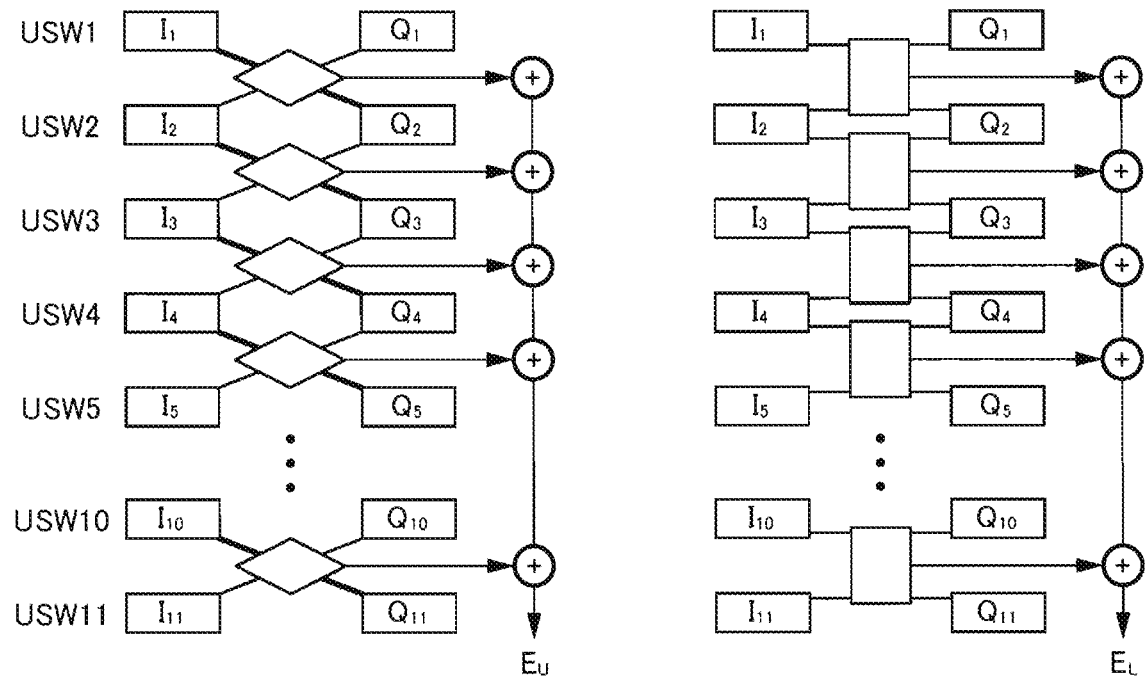
FIGS. 7A and 7B are model diagrams of a flow velocity derivation algorithm of the ultrasonic diagnostic device in a case where ultrasonic pulse transmission/reception numbers N=11.
Figure 7B:
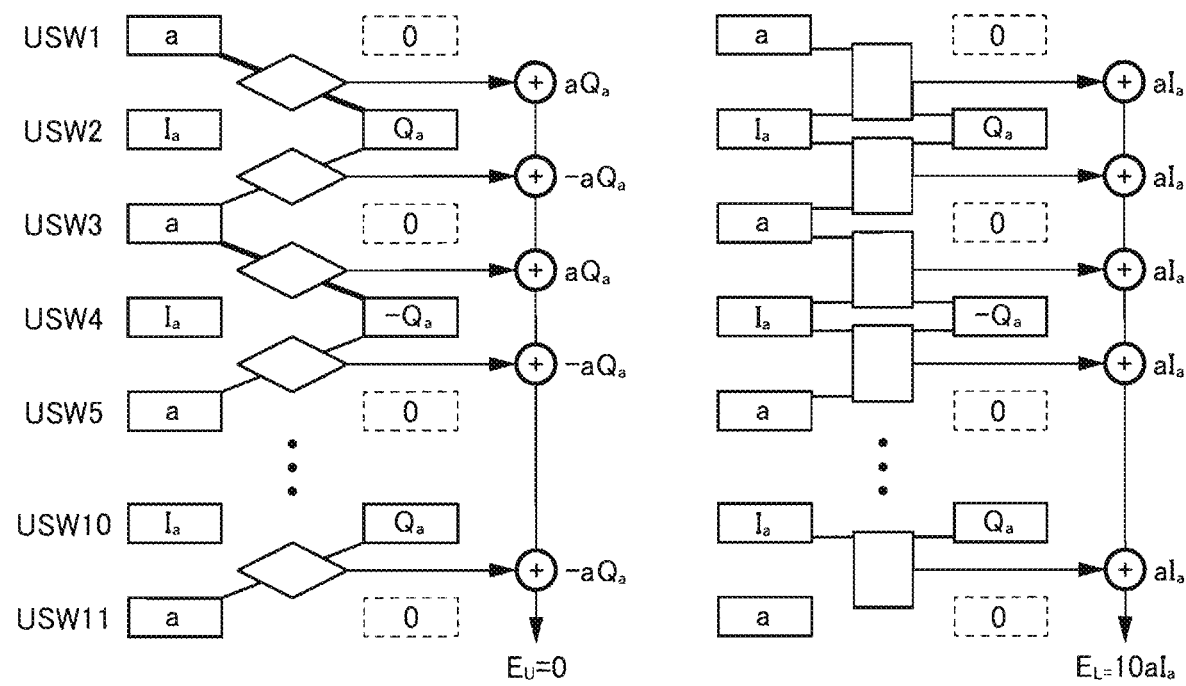

FIG. 7A is a model diagram of the flow velocity derivation algorithm of the ultrasonic diagnostic device 104 in the case where the ultrasonic pulse transmission/reception numbers N=11.

FIG. 7E is a view showing a result of the flow velocity estimation in the ultrasonic diagnostic device 104, in a state where two conditions shown Equation (16) and Equation (18) are all satisfied.

In FIG. 7E, $E_L$ is a value satisfying the following Table 2.

TABLE 2

$$\begin{cases} \text{when } 0 \leq \xi_0 \leq \frac{\lambda}{8} & E_L \geq 0 \\ \text{when } \frac{\lambda}{8} \leq \xi_0 \leq \frac{3\lambda}{8} & E_L \leq 0 \end{cases}$$

$E_U = 0$ no matter what value $E_L$ is. Thus, for a vector with $E_L$ as the real axis and $E_U$ as the imaginary axis, if $E_L$ is a positive value, the vector will be a vector directed to the positive direction on the real axis, and the estimated flow velocity value will be 0. On the other hand, if $E_L$ is a negative value, the vector will be a vector directed to the negative direction on the real axis, and the estimated flow velocity value will be a positive maximum value or a negative maximum value (a maximum flow velocity value determined by the Nyquist frequency).

In other words, the following conclusion can be derived.

<1> Condition that $E_L$ becomes a positive value (in the case where the vibration amplitude caused by the shear elastic wave satisfies "$0 \leq \xi_0 \leq \lambda/8$")

The part of 0 flow velocity will appear on the shear elastic wave detection image when the phase of the vibration amplitude comes to positions of 0° and 180°.

<1> Condition that $E_L$ becomes a negative value (in the case where the vibration amplitude caused by the shear elastic wave satisfies "$\lambda/8 \leq \xi_0 \leq 3\lambda/8$")

The part of maximum flow velocity will appear on the shear elastic wave detection image when the phase of the vibration amplitude comes to positions of 0° and 180°.

The above conditions show that, if the amplitude of the shear elastic wave is set to a value satisfying Equation (2), when the phase of the vibration amplitude caused by the shear elastic wave comes to positions of 0° and 180°, striped pattern will appear on the shear elastic wave detection image. The above two conditions are referred to as "amplitude condition" hereinafter.

When the shear elastic wave is propagating in the tissue, the phase (0° and 180°) of the shear elastic wave can be estimated by extracting the aforesaid characteristic part from the color flow image outputted by the ultrasonic diagnostic device 104. Since the parts of the shear elastic wave having the same phase correspond to reproducing the wave front of the shear elastic wave, the wave front of the shear elastic wave can be reproduced from the color flow image by this method.

This method is for imaging the shear elastic wave, and focuses on a fact that when Equation (1)=Equation (19) is satisfied (which is the frequency condition for imaging the shear elastic wave on the ultrasonic diagnostic device 104), the estimation algorithm of the ultrasonic diagnostic device 104 becomes a digital filter for detecting phases 0° and 180° of the shear elastic wave.

In other words, when applying a vibration with a frequency of n/4 (n represents an odd number equal to or larger than 1) to the object-to-be-measured with respect to the burst frequency corresponding to the repetition cycle of the ultrasonic pulse, the shear elastic wave will appear as a striped pattern on the ultrasonic diagnostic device 104.

The frequency condition for imaging the shear elastic wave on the ultrasonic diagnostic device 104 is theoretically expressed as Equation (1)=Equation (19); however, actually the frequency of the shear elastic wave does not have to match the frequency condition of the shear elastic wave described above. If the frequency of the vibration becomes close to the frequency condition, the parts where the flow velocity value becomes maximum value or 0 will appear on the display 109 of the ultrasonic diagnostic device 104; therefore, even in such a case, the wave front (the striped pattern) of the shear elastic wave can be reproduced on the ultrasonic diagnostic device 104 by this method. The allowable frequency range in which the wave front of the shear elastic wave can be reproduced on the ultrasonic diagnostic device 104 is ±10 Hz at a maximum. As long as the frame rate of the ultrasonic image is a constant, the allowable frequency range does not change even if the burst frequency changes. If more deviation of the frequency occurs, the striped pattern will not be able to be reproduced on the ultrasonic diagnostic device 104. In the case where a vibration with a frequency matching the allowable frequency range is applied, the moving speed of the striped pattern displayed on the ultrasonic diagnostic device 104 will change in accordance with the change of the frequency.

Further, when a frequency of integral multiple of the frame rate of the ultrasonic diagnostic device 104 exists in the frequency range of the shear elastic wave, it looks as if the striped pattern displayed on the ultrasonic diagnostic device 104 is still at the frequency of integral multiple of the frame rate. In the case where it looks as if the striped pattern is still, if changing the frequency of the vibration from such frequency, the moving direction of the striped pattern will change in accordance with the increasing/decreasing direction of frequency.

For example, in the case where the frequency of the frame rate of the ultrasonic diagnostic device 104 is 10 Hz and the burst frequency is 365 Hz, the frequency of the shear elastic wave will be 91.25 Hz when n=1, or 273.75 Hz when n=2. In the case where the frequency of the shear elastic wave is 273.75 Hz, the striped pattern can be reproduced on the ultrasonic diagnostic device 104 in a range of ±5 Hz, i.e., within a range from 268.75 Hz to 278.75 Hz. Particularly, since 270 Hz, which is integral multiple of the frame rate, exists in such a frequency range, it looks as if the striped pattern displayed on the ultrasonic diagnostic device 104 is still when the frequency of the shear elastic wave is 270 Hz.

<Propagation Velocity Estimation of Shear Elastic Wave Based on Wave Front of Shear Elastic Wave>

When the frequency condition is satisfied, the estimated flow velocity value shows maximum value or 0 at two places near 0° and 180° of the phase of the shear elastic wave. In other words, the wavelength of the shear elastic wave can be obtained by performing image processing to extract such part, and thereby the propagation velocity of the shear elastic wave can be estimated. To be specific, the following two methods can be used.

Method 1 (Estimation Method Based on Spatial Distribution of Flow Velocity)

Two-dimensional autocorrelation of an image on which the wave front of the shear elastic wave is recorded is calculated. A distance d over which a phase rotation caused by the propagation of the shear elastic wave becomes 180° can be obtained based on the peak or the correlation or the gravity center position of correlation value. Thus, the propagation velocity $v_s$ of the shear elastic wave can be calculated using the following Equation (28). More strictly, the distance d needs to be corrected with respect to the interval between the striped pattern appearing on the screen of the display device 108 when considering the delay of the transmission time inherent to the ultrasonic diagnostic device 104 occurring when transmitting the ultrasonic pulse from the ultrasonic probe 103; and details about such correction is omitted herein.

[Mathematical Expression 22]

$$V_s = 2d^* f_b \quad (28)$$

Method 2 (Estimation method based on movement of wave fronts of two past frames.

Two-dimensional mutual correlation functions of two images separated from each other by time T are calculated. A distance over which a phase rotation caused by the propagation of the shear elastic wave becomes 180° can be obtained based on the peak or the correlation or the gravity center position of correlation value. Thus, the propagation velocity $v_s$ of the shear elastic wave can be calculated using the above Equation (28).

[Configuration of CFI Image Processing Device 107]

Figure 8:
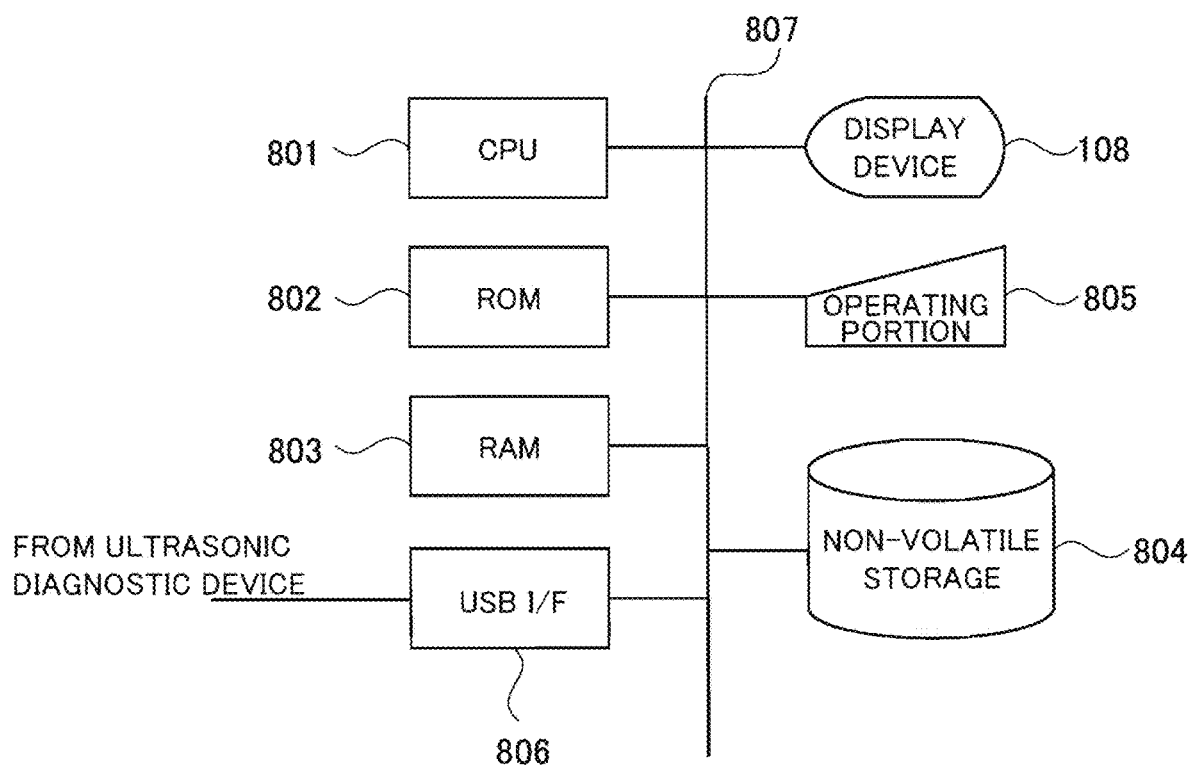
FIG. 8 a block diagram showing a hardware configuration of a CFI image processing device.

FIG. 8 is a block diagram showing a hardware configuration of the CFI image processing device 107.

The CFI image processing device 107 configured by a widely known personal computer is formed by connecting a CPU 801, a ROM 802, a RAM 803, a non-volatile storage 804 (such as a hard disk device), display device 108, an operating portion 805, and a USB interface 806 (referred to as "USE I/F" in FIG. 8) to a bus 807.

Figure 9:
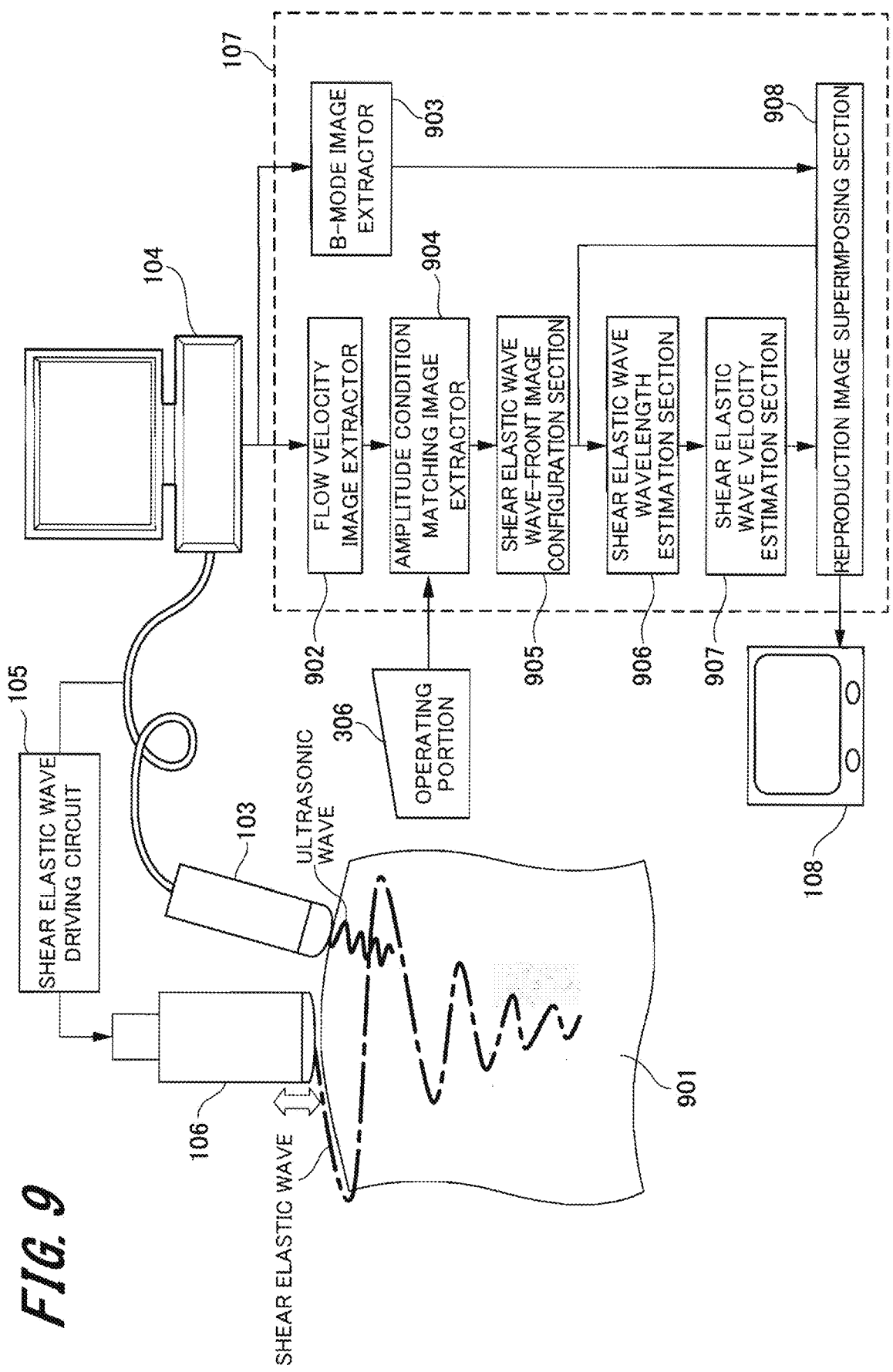
FIG. 9 is a functional block diagram of the CFI image processing device.

FIG. 9 is a functional block diagram of the CFI image processing device 107.

The ultrasonic probe 103 emits an ultrasonic pulse to a body tissue 901 of the subject 102, and receives the ultrasonic pulse.

Similarly, the vibration exciter 106 driven by the shear elastic wave driving circuit 105 applies a shear elastic wave to the body tissue 901.

The ultrasonic diagnostic device 104 outputs the color flow image.

The CFI image processing device 107 is formed by causing the widely known personal computer described above with reference to FIG. 8 to execute a program that allows the personal computer to act as the CFI image processing device 107.

Digital image data (which is not only color flow image data, but also shear elastic wave detection image data) outputted from the ultrasonic diagnostic device 104 is inputted to a flow velocity image extractor 902 and a B-mode image extractor 903.

The flow velocity image extractor 902 extracts the color flow image data from the digital image data. The flow velocity image extractor 903 extracts the B-mode image data from the digital image data. In many cases, the digital image data outputted from the ultrasonic diagnostic device 104 has a display area of the color flow image appearing in a center portion of the black-and-white B-mode image. Thus, the flow velocity image extractor 902 and the B-mode image extractor 903 can be integrally configured by extracting the color portion with the help of coordinate information. In other words, the flow velocity image extractor 902 and the B-mode image extractor 903 are in an exclusive relationship.

The color flow image data outputted from the flow velocity image extractor 902 is inputted to an amplitude condition matching image extractor 904. The amplitude condition matching image extractor 904 extracts components of the image data that matches the amplitude condition (i.e., components of the image data that satisfies Equation (2)) from the color flow image data. The amplitude condition is provided to the amplitude condition matching image extractor 904 by inputting frequency information of the ultrasonic probe 103 and shear elastic wave driving circuit 105 (synchronous oscillator 208) from the operating portion 805. To be specific, for example, if the amplitude is a value matching the amplitude condition, since the maximum flow velocity value appears on the color flow image, the image matching the amplitude condition is extracted with the fact that the maximum flow velocity value appears on the image as a criterion.

The amplitude condition matching image data outputted from the amplitude condition matching image extractor 904 is inputted to a shear elastic wave wave-front image configuration section 905. The shear elastic wave wave-front image configuration section 905 reproduces the wave front of the shear elastic wave from the amplitude condition matching image data outputted by the amplitude condition matching image extractor 904. To be specific, for example, a flow velocity value equal to half of the maximum flow velocity is used as a threshold, and the wave front of the shear elastic wave is reproduced by performing a processing so that if the flow velocity value is equal to or larger than the threshold, the flow velocity value will be treated as 1; and if the flow velocity value is smaller than the threshold, the flow velocity value will be treated as 0.

The shear elastic wave wave-front image data outputted from the shear elastic wave wave-front image configuration section 905 is inputted to a shear elastic wave wavelength estimation section 906. The shear elastic wave wavelength estimation section 906 uses two-dimensional correlation from the shear elastic wave wave-front image data to estimate the wavelength of the shear elastic wave in the shear elastic wave wave-front image data.

The shear elastic wave wavelength data outputted from the shear elastic wave wavelength estimation section 906 is inputted to a shear elastic wave velocity estimation section 907. The shear elastic wave velocity estimation section 907 estimates the propagation velocity of the shear elastic wave from the shear elastic wave wavelength data. The estimated propagation velocity data of the shear elastic wave is plotted into lines like contour lines of a map, for example.

The B-mode image data outputted from the B-mode image extractor 903, the shear elastic wave wave-front image data outputted from the shear elastic wave wave-front image configuration section 905, and the propagation velocity data of the shear elastic wave outputted from the shear elastic wave velocity estimation section 907 are inputted to a reproduction image superimposing section 908. The reproduction image superimposing section 908 superimposes the B-mode image data, the shear elastic wave wave-front image data, and the propagation velocity data of the shear elastic wave onto each other to reconfigure integral image data.

The image data outputted from the reproduction image superimposing section 908 is inputted to the display device 108 where a shear elastic wave display image including the striped pattern of the shear elastic wave is displayed.

Figure 10:
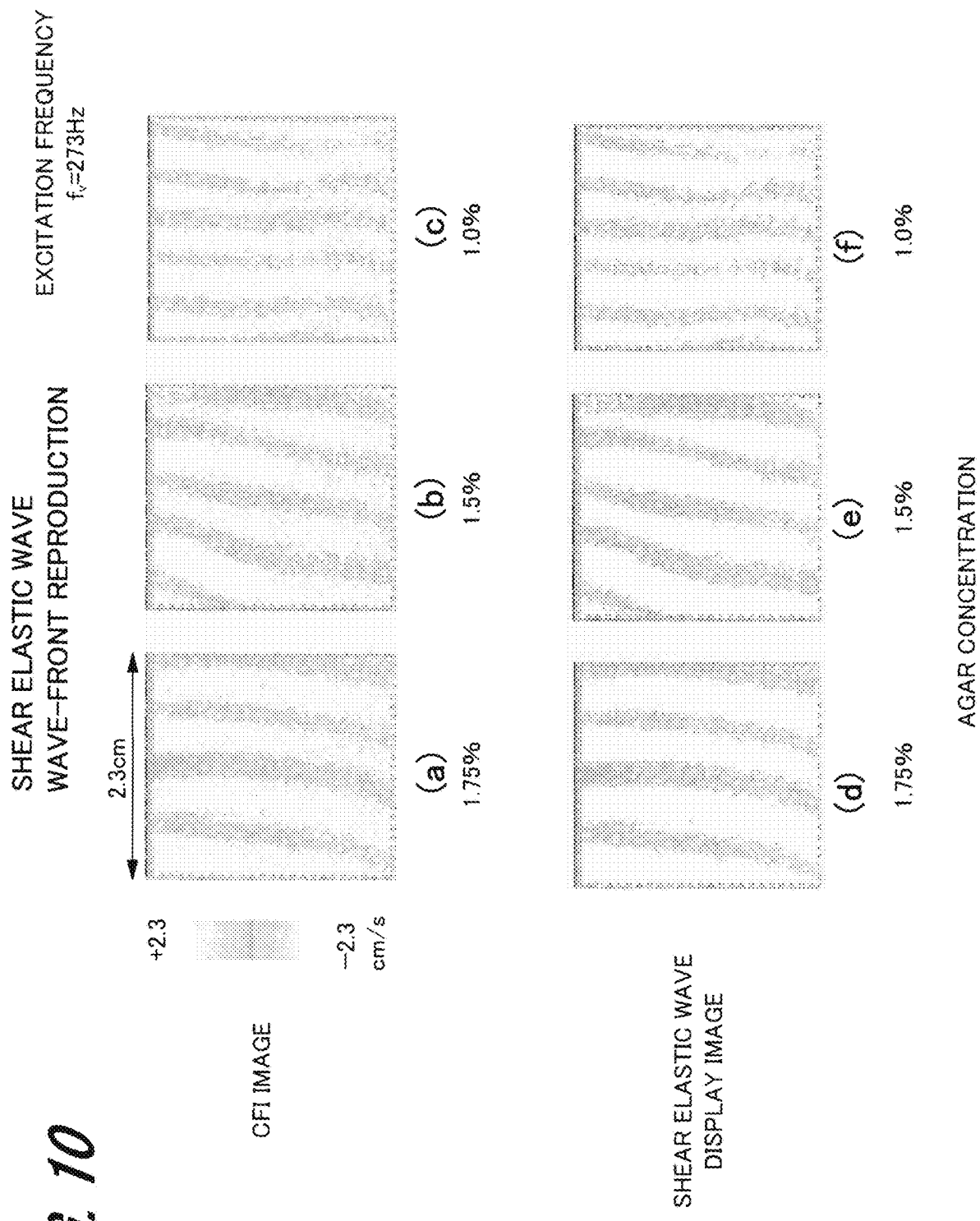
FIG. 10 is a view showing examples of a shear elastic wave detection image displayed on the ultrasonic diagnostic device and a shear elastic wave display image displayed on a display device of the ultrasonic imaging system of the present embodiment.

FIG. 10 is a view showing examples of e shear elastic wave detection image displayed on the ultrasonic diagnostic device 104 and the shear elastic wave display image displayed on the display device 108 of the ultrasonic imaging system 101 of the present embodiment. The images shown in FIG. 10 are shear elastic wave detection images and shear elastic wave display images obtained when measuring a pseudo living body phantom with the ultrasonic imaging system 101, wherein the pseudo living body phantom is created by mixing graphite powder, which scatters the ultrasonic wave, into agar. Three pseudo living body phantoms with different agar concentration are created. The three pseudo living body phantoms have an agar concentration of 1.75%, 1.5% and 1% respectively.

Image (a) of FIG. 10 is a shear elastic wave detection image obtained when the agar concentration is 1.75%.

Image (b) of FIG. 10 is a shear elastic wave detection image obtained when the agar concentration is 1.5%.

Image (c) of FIG. 10 is a shear elastic wave detection image obtained when the agar concentration is 1%.

Image (d) of FIG. 10 is a shear elastic wave display image obtained when the agar concentration is 1.75%.

Image (e) of FIG. 10 is a shear elastic wave display image obtained when the agar concentration is 1.5%.

Image (f) of FIG. 10 is a shear elastic wave display image obtained when the agar concentration is 1%.

It can be known from images (a), (b) and (c) of FIG. 10 that, although each shear elastic wave detection image includes much noise, a characteristic striped pattern caused by the shear elastic wave appears on the image.

Higher agar concentration means the phantom has higher stiffness, and therefore the shear elastic wave has higher the propagation velocity. In other words, the shear elastic wave has longer wavelength. Conversely, lower agar concentration means the phantom has lower stiffness, and therefore the shear elastic wave has lower propagation velocity. In other words, the shear elastic wave has shorter wavelength. The results of FIG. 10 show that the difference in stiffness of the agar can be discriminated as the difference in wavelength of the shear elastic wave.

Further, it can be known images (d), (e) and (f) of FIG. 10 that, in a shear elastic wave display image, since noise component is remarkably removed compared with the shear elastic wave detection image, the intervals of the striped pattern can be more clearly recognized. Incidentally, it is preferred that, when measuring the intervals of the striped Pattern, the intervals of white (or light-colored) parts are measured. This is because the parts where the flow velocity is (the black or light-colored parts) are susceptible to the effect of the noise, and therefore it is expected to reduce the error by measuring the parts which show maximum flow velocity.

Further, the striped pattern actually moves on the screen, although such movement cannot be recognized in images shown in FIG. 10 as these images are still images. The moving speed varies depending on the frequency difference and phase difference between the frequency of the shear elastic wave satisfying Equation (1) and the frequency of the shear elastic wave actually supplied from the vibration exciter 106, and the phase difference. The transmission direction of the shear elastic wave can be visually recognized from the moving direction of the striped pattern. Further, the transmission direction of the shear elastic wave can be obtained as vector data by performing image analysis on the moving direction of the striped pattern. The transmission direction of the shear elastic wave can be visualized by displaying the vector data showing the transmission direction of the shear elastic wave as an illustration of arrow marks, for example, on the display device 108. Since the transmission direction of the shear elastic wave can be visualized, various abnormalities in body tissue can be clearly estimated. For example, tissue boundary surface can be clearly visualized from the refraction of the shear elastic wave. Further, in the case where tissue adhesion occurs, the same vibration is transmitted by two adherent tissues. Thus, information such as the facts that refraction is unlikely to occur, that the propagation direction does not change, and the like can be obtained. Further, in the case of diseases such liquefaction degeneration like fibroid, the propagation direction of the shear elastic wave will become locally uneven. Thus, the fact that the tissue is liquefaction degeneration can be clearly known from the propagation direction of the shear elastic wave.

The aforesaid embodiment includes the following applications.

(1) In the aforesaid embodiment, the ultrasonic imaging system 101 is built in which the existing ultrasonic diagnostic device 104 is used in its entirety; however, the present invention also includes a configuration in which the ultrasonic diagnostic device 104 includes the arithmetic function of the CFI image processing device 107.

(2) In the aforesaid embodiment, in order to further improve the clarity of the shear elastic wave display image, a shear elastic wave with two or more frequencies may be used to vibrate the object-to-be-measured.

In the reproduction of the wave front of the shear elastic wave by the ultrasonic diagnostic device 104, when the frequency matching the frequency condition satisfies the amplitude condition, characteristic flow velocity value is estimated near the phases 0° and 180° of the shear elastic wave; and such fact is used to reproduce the wave front of the shear elastic wave.

In other words, when the displacement amplitude becomes the data row shown in FIG. 4 with respect to ultrasonic pulse, the wave front of the shear elastic wave can be reproduced.

The pattern of the displacement amplitude for each ultrasonic pulse shown in FIG. 4 can be achieved not only in the case where there is one shear elastic wave with single frequency, but also in the case where a plurality of shear elastic waves matching the frequency condition are excited simultaneously while the summed vibration amplitudes satisfy the condition of FIG. 4.

In the excitation of the shear elastic wave with one frequency, in order to reach a maximum flow velocity value, the following Equation (29) is required to be satisfied.

[Mathematical Expression 23]

$$\frac{\lambda}{8} \le \xi_0 \le \frac{3\lambda}{8} \quad (29)$$

However, in the case where the plurality of shear elastic waves matching the frequency condition are excited simultaneously, the "sum of amplitudes" may satisfy the above condition when the ultrasonic pulse is being transmitted.

When using such fact, if the initial phases of the displacement amplitudes of two shear elastic waves (for example, one is a shear elastic wave whose vibration amplitude is $\xi_{0,0}$ at frequency m=0, and the other is a shear elastic wave whose vibration amplitude is $\xi_{0,1}$ at frequency m=1 with respect to the frequency condition Equation (19), which is equal to Equation (1)) are selected so that the displacement amplitudes of the two shear elastic waves at maximum amplitudes are in phase and overlapped with each other, the amplitude condition when the flow velocity becomes maximum can be rewritten into the following Equation (30).

[Mathematical Expression 24]

$$\frac{\lambda}{8} \le \xi_{0,0} + \xi_{0,1} \le \frac{3\lambda}{8} \quad (30)$$

The following are advantages of using the plurality of frequencies simultaneously.

<1> The higher the frequency of the shear elastic wave is, an image with the higher spatial resolution can be obtained; however, if the frequency of the shear elastic wave is increased, attenuation of the shear elastic wave will increase, and therefore it is difficult to obtain large vibration amplitude, so that it becomes difficult to satisfy the amplitude condition in which the estimated flow velocity becomes maximum. However, if a low frequency (vibration amplitude: $\xi_{0,0}$) with less attenuation and a high frequency (vibration amplitude: $\xi_{0,1}$) for imaging are excited simultaneously, since the amplitude condition is eased as Equation (30), <2> Since simultaneously exciting the shear elastic waves with a plurality of frequencies with the phases matched each other corresponds to previously biasing the vibration amplitudes, even the wave fronts of the shear elastic waves with high frequencies and small vibration amplitudes can be reproduced with high sensitivity by using the present method of simultaneously exciting the plurality of frequencies.

(3) In the aforesaid embodiment, the object-to-be-measured is excited with the vibration exciter 106; however, the means for generating a shear elastic wave is not limited to the vibration exciter 106. The ultrasonic probe 103 may also be integrated with the vibration exciter 106.

It is also possible to cause one of the plurality of ultrasonic transducers 202 contained in the ultrasonic probe 103 to generate a strong ultrasonic wave using the acoustic radiation pressure method to thereby generates a shear elastic wave with the ultrasonic probe 103 alone by means of space division.

Further, it is also possible to alternately change over between the time while the strong ultrasonic wave is generated using the acoustic radiation pressure method and the time while the ultrasonic pulse for image reproduction is generated to thereby generates a shear elastic wave with the ultrasonic probe 103 alone by means of time division.

In other words, a concept of "shear elastic wave generator" is used a generic concept of the means for generating the shear elastic wave.

In the present embodiment, the ultrasonic imaging system 101 is described.

The existing ultrasonic diagnostic device 10 is used to obtain a color flow image of a target object whose stiffness is to be measured. At this time, the vibration exciter 106 applies micro vibration with a frequency of n/4 (n represents an odd number equal to or larger than 1) to the target object with respect to the burst frequency of the ultrasonic pulse to generate a shear elastic wave. As a result, a striped pattern corresponding to the stiffness of the target object caused by the shear elastic wave appears on the display 109 of the ultrasonic diagnostic device 104 as a shear elastic wave detection image. Further, a shear elastic wave display image with reduced noise can be obtained by performing a predetermined arithmetic processing on shear elastic wave detection image data.

Thus, according to the present embodiment, the stiffness of the object-to-be-measured can be easily measured by adding a relatively simple device.

The embodiment of the present invention is described as above; however, it is to be understood that the present invention is not limited to the embodiment described above, and various modifications and applications can be made without departing from the spirit described in the claims of the present invention.

For example, in the aforesaid embodiment, the configurations of the device and system are described in detail and concrete manner so that the present invention is easily understandable; however, the aforesaid configurations do not have to be fully included. Further, configurations of one embodiment can be partly substituted with configurations of other embodiments, and configurations of one embodiment can be added with a configuration(s) of other embodiments. Further, configurations of one embodiment can be partly omitted, or added with other configuration(s), or substituted with other configurations.

Further, the aforesaid each configuration, function, processor and the like can be partly or entirely achieved by hardware by being designed using an integrated circuit, for example. Further, the aforesaid each configuration, function and the like can be achieved by software whose processor explains and executes a program that achieves respective functions. Information such as the program, tables, files and the like for achieving each function can be stored in a volatile or non-volatile storage, such as a memory, a hard disk, a SSD (solid state drive) or the like, or a recording medium, such as an IC card, an optical disk or the like.

Further, a control line and an information line are shown because it is required for description, but the product does not necessarily show the control line and information line. It can be considered that almost all configurations are actually connected with each other.

REFERENCE SIGNS LIST 101 ultrasonic imaging system
102 subject
103 ultrasonic probe
104 ultrasonic diagnostic device
105 shear elastic wave driving circuit
106 vibration exciter
107 CFI image processing device
108 display device
109 display
201 oscillator
202 ultrasonic transducer
203 frequency divider
204 first multiplexer
205 second multiplexer
206 first multiplier
207 second multiplier
208 synchronous oscillator
209 first A/D converter
210 90° phase shifter
211 second A/D converter
212 arithmetic processor
301 first sample buffer
302 second sample buffer
303 B-mode image processor
304 image processor
305 noise removal arithmetic processor
306 flow velocity data arithmetic section
801 CPU
802 ROM
803 RAM
804 non-volatile storage
805 operating portion
806 USB interface
807 bus
901 body tissue
902 flow velocity image extractor
903 B-mode image extractor
904 amplitude condition matching image extractor
905 shear elastic wave wave-front image configuration section
906 shear elastic wave wavelength estimation section
907 shear elastic wave velocity estimation section
908 reproduction image superimposing section

The invention claimed is:

1. An ultrasonic imaging system comprising:
an ultrasonic image forming device configured to generate an ultrasonic pulse for measuring an inside structure of an object-to-be-measured in a non-invasive manner, emit the ultrasonic pulse from an ultrasonic probe, and receive a reflected signal in response to the ultrasonic pulse emitted; and
a shear elastic wave generator configured to apply a vibration with a predetermined frequency to the object-to-be-measured, to thereby generate a shear elastic wave causing an image of a striped pattern depending on a stiffness of the object-to-be-measured, wherein a first position of the ultrasonic probe and a second position of the shear elastic wave generator are located differently from each other so that the ultrasonic pulse from the ultrasonic probe and the vibration from the shear elastic wave generator are transmitted to the object-to-be-measured from different positions, the ultrasonic image forming device images the stiffness of the object-to-be-measured based on the vibration and the ultrasonic pulse for diagnosing a disease, wherein, the shear elastic wave generator applies the vibration with a frequency of n/4, wherein n represents an odd number equal to or greater than 1, as a center frequency to the object-to-be-measured, with respect to a burst frequency corresponding to a repetition cycle of the ultrasonic pulse.

2. The ultrasonic imaging system according to claim 1, wherein the shear elastic wave generator applies the vibration to the object-to-be-measured, wherein the predetermined frequency of the vibration falls in a range of +10 Hz at most with respect to the center frequency.

3. The ultrasonic imaging system according to claim 2 further comprising:
   a color flow image (CFI) processing device configured to receive input data of a color flow image outputted from the ultrasonic image forming device and output image data including information about the stiffness of the object-to-be-measured.

4. The ultrasonic imaging system according to claim 3, wherein the CFI processing device is further configured to estimate the stiffness of the object-to-be-measured by estimating, based on the color flow image, a wavelength of a shear elastic wave generated in the object-to-be-measured based on a vibration frequency of the shear elastic wave generator.

5. The ultrasonic imaging system according to claim 4, wherein the CFI processing device is further configured to include information about a propagation direction of the shear elastic wave by estimating the wavelength of the shear elastic wave.

* * * * *